(12) United States Patent
Laurence et al.

(10) Patent No.: US 9,535,175 B2
(45) Date of Patent: Jan. 3, 2017

(54) SCATTER REJECT METHOD VIA ENERGY CALIBRATION

(71) Applicant: KONINKLIJKE PHILIPS N.V., Eindhoven (NL)

(72) Inventors: Thomas Leroy Laurence, North Royalton, OH (US); Sharon Xiaorong Wang, Highland Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/915,376

(22) PCT Filed: Sep. 16, 2014

(86) PCT No.: PCT/IB2014/064539
§ 371 (c)(1),
(2) Date: Feb. 29, 2016

(87) PCT Pub. No.: WO2015/040535
PCT Pub. Date: Mar. 26, 2015

(65) Prior Publication Data
US 2016/0209524 A1    Jul. 21, 2016

Related U.S. Application Data

(60) Provisional application No. 61/878,738, filed on Sep. 17, 2013.

(51) Int. Cl.
*A61B 6/00* (2006.01)
*G01T 1/164* (2006.01)
*G01T 1/20* (2006.01)
*G01T 7/00* (2006.01)
*G01T 1/29* (2006.01)
*A61B 6/03* (2006.01)

(52) U.S. Cl.
CPC ............ *G01T 1/2985* (2013.01); *A61B 6/037* (2013.01); *G01T 1/1647* (2013.01); *G01T 7/005* (2013.01)

(58) Field of Classification Search
CPC ..... A61B 6/037; G01T 1/1647; G01T 1/2985; G01T 7/005
See application file for complete search history.

(56) References Cited

U.S. PATENT DOCUMENTS

| | | |
|---|---|---|
| 7,479,639 B1 | 1/2009 | Shahar |
| 7,714,291 B2 | 5/2010 | Thielemans |
| 7,894,568 B2 | 2/2011 | Ziegler |
| 7,915,578 B2 | 3/2011 | Case |
| 2004/0054248 A1 | 3/2004 | Kimchy |
| 2010/0193696 A1 | 8/2010 | Blevis |
| 2011/0012014 A1 | 1/2011 | Livne |
| 2011/0105887 A1* | 5/2011 | Gagnon ............... A61B 6/037 600/410 |
| 2011/0142367 A1 | 6/2011 | Stearns |

* cited by examiner

Primary Examiner — Mark R Gaworecki

(57) ABSTRACT

A medical nuclear imaging system (10) and corresponding method (100) are provided. A plurality of pixels (20, 24) detect radiation events and estimate the energy of the detected radiation events. A memory (58) stores a plurality of energy windows (44), the energy windows corresponding to the pixels. An event verification module (56) windows the radiation event with the energy windows corresponding to the detecting pixels. A reconstruction processor (60) reconstructs the windowed radiation events into an image representation.

15 Claims, 7 Drawing Sheets

SCATTER REJECT METHOD VIA ENERGY CALIBRATION

CROSS REFERENCE TO RELATED APPLICATIONS

This application is the U.S. National Phase application under 35 U.S.C. §371 of International Application No. PCT/IB2014/064539, filed Sep. 16, 2014, published as WO 2015/040535 on Mar. 26, 2015, which claims the benefit of U.S. Provisional Patent Application No. 61/878,738 filed Sep. 17, 2013. These applications are hereby incorporated by reference herein.

The present application relates generally to nuclear imaging. It finds particular application in conjunction with energy calibration in positron emission tomography (PET), and will be described with particular reference thereto. However, it is to be understood that it also finds application in other usage scenarios, such as single-photon emission computed tomography (SPECT), and is not necessarily limited to the aforementioned application.

In many clinical applications of three-dimensional (3D) PET imaging, such as cancer treatment staging (oncology), an accurate quantitative measurement of a patient's standardized uptake values (SUV) is critical. A 3D PET scanner yields high sensitivity, but corrections for attenuation, scatter and randoms must be performed by reconstruction to yield accurate SUV measurements. At typical oncology study data rates, scatter events are about 30% of total events. Rather than identify specific data as attributed to scatter, a statistical correction to the data set is employed during the reconstruction process. Because of the statistical nature of the data that inherently has "noise", removal of scatter is not perfect and is one of the sources of SUV inaccuracies. Without a significant improvement in scatter rejection, the quantitative analysis accuracy is compromised.

Historically, PET systems have used a fixed lower level discriminator (LLD) energy threshold, such as 439 kiloelectron-volts (keV), to minimize scatter events in the processing pipeline. While this approach is simple, it has the shortcoming of accepting some scatter events as the energy resolution is improved since the LLD is fixed and not optimized and/or tightened to discriminate against Compton scatter events. Referring to FIG. 1, a graph of scatter fraction versus energy resolution for known PET systems is provided. As can be seen, the systems with improved (i.e., lower) energy resolution (E-res) values generally result in increased scatter fractions since a fixed LLD allows more scatter to be passed.

One way of rejecting more scatter events is to optimize the LLD of an energy window for an energy spectrum. FIG. 2 shows an energy spectrum. The centroid of the energy peak is 511 keV (i.e., the known energy of the gamma rays created in a PET annihilation event). Further shown are the LLD and the upper level discriminator (ULD) of an energy window, which typically removes stray radiation from other sources. Current PET systems employ one energy window for all pixels in the whole system. This one-size-fits-all window unavoidably allows more scatter events for pixels with narrower energy spectrums, as shown in FIG. 2, where the ULD is too far to the right. Further, this one-size-fits-all window unavoidably rejects true events for pixels with wider energy spectrums.

Due to variations in crystals and sensors, the energy spectrums of pixels of PET systems typically vary. Hence, the energy resolutions of pixels of PET systems vary. The variation in energy resolution can be as large as 40% or larger over the whole system. The present application provides an improvement to the traditional approach to scatter rejection (i.e., using a fixed energy window) which is particularly advantageous for edge pixels, where the energy resolutions are systemically higher.

In accordance with one aspect, a medical nuclear imaging system is provided. The system includes a plurality of pixels which detect radiation events and generate an energy spectrum in response to the detected radiation events and estimate the energy of the detected radiation events. The system further includes a memory which stores a plurality of energy windows, the energy windows corresponding to the pixels. Even more, the system includes an event verification module which windows the radiation events with the energy windows corresponding to the detecting pixels. Moreover, the system includes a reconstruction processor which reconstructs the windowed radiation events into an image representation.

In accordance with another aspect, a medical nuclear imaging method includes detecting radiation events by a plurality of pixels, estimating the energy of the detected radiation events, and receiving a plurality of energy windows. The pixels correspond to the energy windows. The method further includes windowing the radiation event with the energy windows corresponding to the detecting pixels and reconstructing the windowed radiation events into an image representation.

In accordance with another aspect, a medical system for calibrating a nuclear imaging system is provided. The medical system includes at least one processor programmed to receive a plurality of energy spectra for gamma ray detectors of the imaging system. The energy spectra correspond to different pixels of the detectors. The at least one processor is further programmed to fit the energy spectra with Gaussian curves, fit trend lines to both sides of the Gaussian curves of the energy spectra, and determine lower level discriminators (LLDs) and upper level discriminators (ULDs) from the fitted trend lines. The LLDs and the ULDs define individual energy windows for the pixels.

One advantage resides in improved scatter rejection in positron emission tomography (PET) imaging.

Another advantage resides in improved image quality in PET imaging.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

In three-dimensional (3D) positron emission tomography (PET) imaging, a big portion of noise comes from the scatter events. Properly rejecting these scatter events before image reconstruction, can improve PET image quality. The present application describes a method that measures the system energy response of individual pixels of a PET system and then determines the optimum energy window for each pixel during energy calibration. When imaging a patient, these optimum energy windows are used to select the true events. This increases the signal to noise ratio and improves image contrast.

Figure 1:
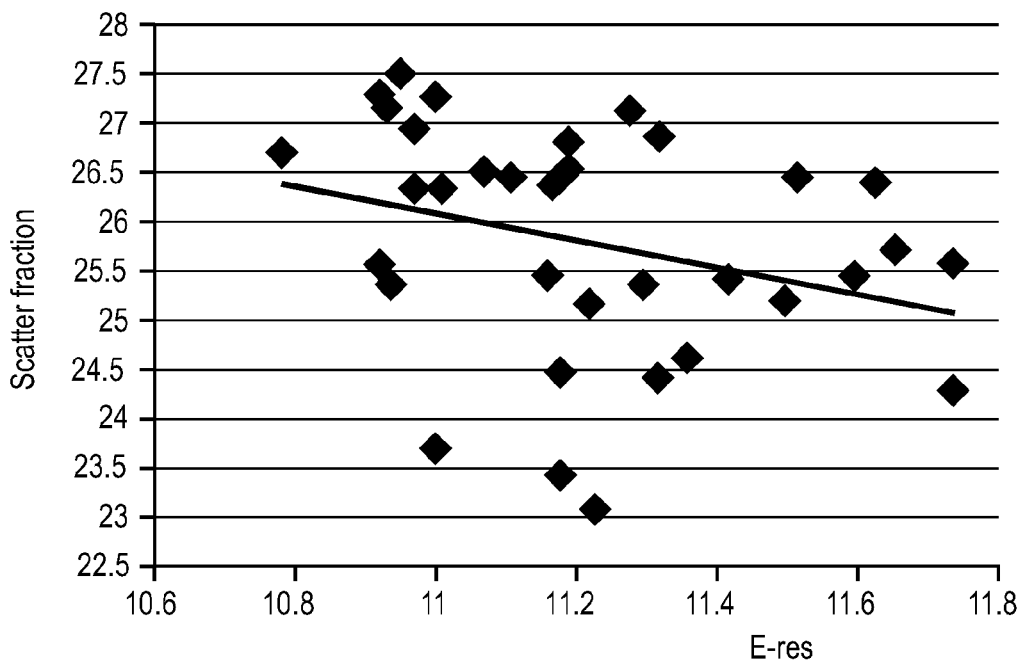
FIG. 1 illustrates a graph of scatter fraction versus energy resolution for positron emission tomography (PET) systems.
Figure 2:
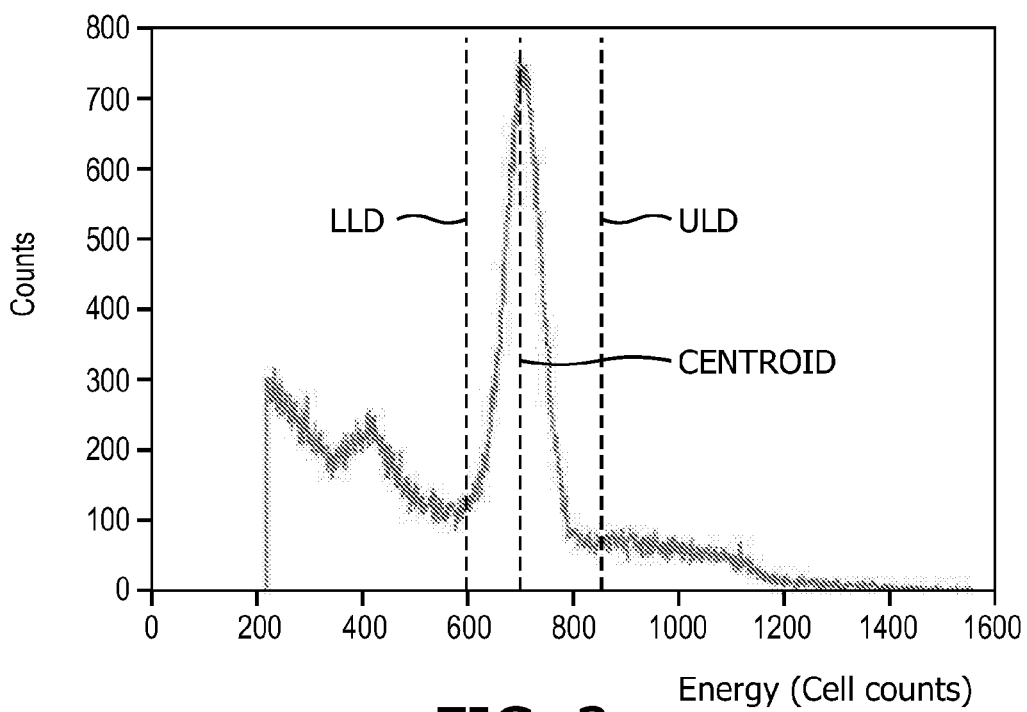
FIG. 2 illustrates an energy spectrum of a pixel and an energy window.
Figure 3:
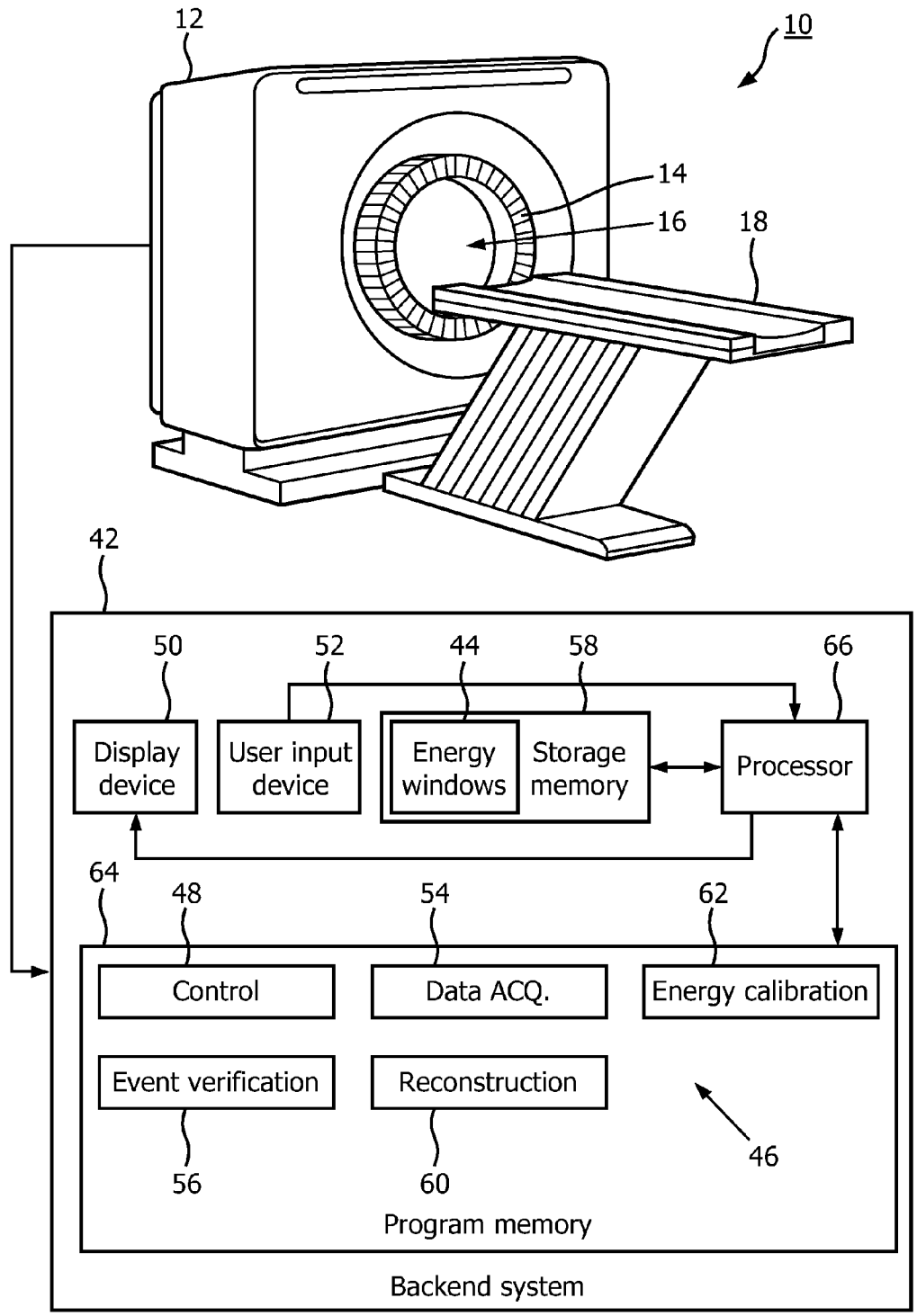
FIG. 3 illustrates a PET imaging system using energy windows for scatter rejection for each pixel.

With reference to FIG. 3, a nuclear imaging system 10, such as the illustrated 3D PET imaging system, includes a nuclear scanner 12, particularly a PET scanner, which generates raw imaging data. The scanner 12 includes detectors 14, typically formed from scintillator crystals and silicon photomultipliers (SiPMs), arranged around a bore of the scanner 12. The bore defines an examination region 16 for receiving a region of interest (ROI), such as a brain, torso, or the like, of a subject to be imaged. The detectors 14 are typically arranged in one or more stationery rings which extend a length of the examination region 16. However, rotatable heads are also contemplated. A motor and drive or the like provides longitudinal movement and vertical adjustment of a subject support 18 in the examination region 16.

Figure 4:
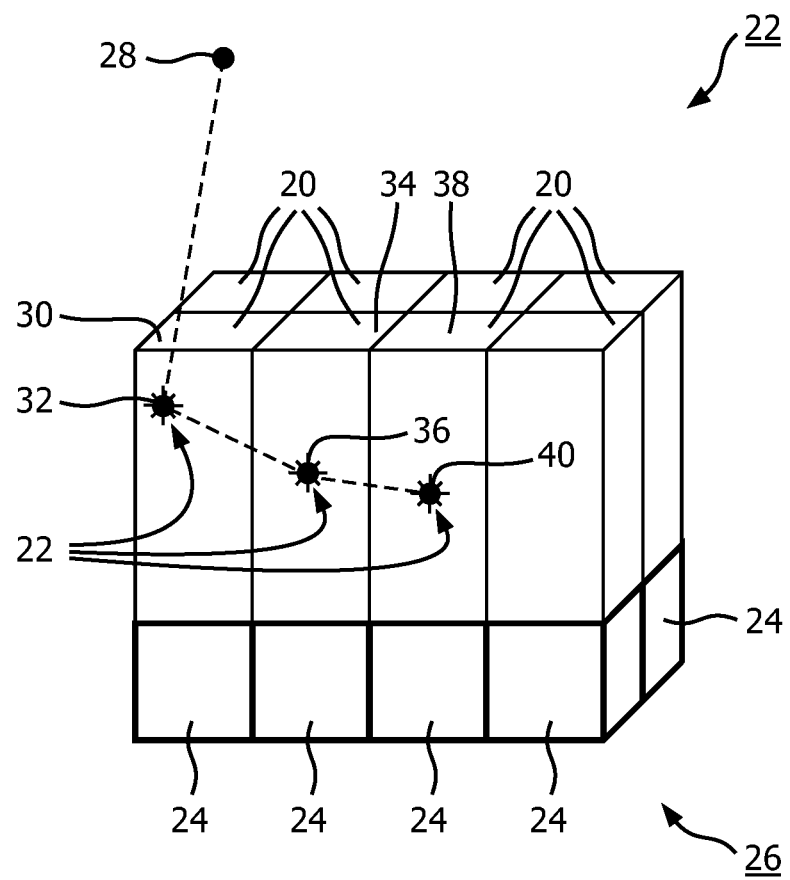
FIG. 4 illustrates a scatter event in scintillation elements of a PET detector.

The detectors 14 detect gamma photons from the examination region 16. With reference to FIG. 4, in the illustrated embodiment, each of the detectors 14 includes one or more scintillators 20 arranged in a grid 22. Further, each of the detectors 14 includes one or more light sensors 24 each optically coupled to a corresponding scintillator and arranged in a grid 26 of like size as the grid 22 of scintillators 20. There is often a one-to-one correspondence between the scintillators 20 and the sensors 24 (as illustrated), but other correspondences are also contemplated. The scintillators 20 receive gamma photons from the examination region 16. As the gamma photons deposit energy in the scintillators 20, the scintillators scintillate and emit light towards the sensors 24. The amount of light created by a scintillation event is directly correlated to the amount of energy deposited. The sensors 24 detect the light emitted by the scintillations 20. Examples of scintillators include sodium iodide doped with thallium (NaI(Tl)), cerium-doped lutetium yttrium orthosilicate (LYSO) and cerium doped lutetium oxyorthosilicate (LSO). Examples of sensors include photomultiplier tubes (PMTS), photodiodes, avalanche photodiodes, and silicon photomultipliers (SiPMs).

In the illustrated example, the scintillators 20 receive a gamma photon 28, which is Compton scattered in a first scintillator 30 and deposits only a portion of its energy in the first scintillator 30, thereby causing the first scintillator 30 to emit a light pulse 32. If the Compton angle is small, very little energy is deposited and the light pulse 32 is very small. However, if the Compton angle is large, then substantially all of the energy is deposited and the light pulse 32 is hard to distinguish from the light pulse 32 that results from all of the energy being deposited. As illustrated, the Compton angle in the first scintillator 30 is very small, whereby the scattered gamma photon 28 has substantially all of its energy and proceeds to a second scintillator 34. If the interaction in the second scintillator 34 deposits all of the remaining energy or has a large Compton angle and deposits almost all of the remaining energy, then the output light pulse 36 will look very similar to an unscattered scintillator event. As illustrated, the scattered gamma photon 28 proceeds to a third scintillator 38, where its remaining energy is deposited, thereby creating a light pulse 40. The sensors 24 detect the scintillation events resulting from the deposition of energy in the three scintillator elements 30, 34, 38.

Referring back to FIG. 3, a backend system 42 determines an individual energy window 44 for each pixel of the detectors 14, such that each pixel has its own energy window. Due to different sensitivities of the pixels, the energy windows 44 vary from one pixel to another. As used herein, a pixel is the smallest area of the detectors 14 to which a measured gamma photon deposition can be localized. For example, where the sensors 24 correspond to SiPMs, each pixel can correspond to one of the pixels of the SiPMs (i.e., one of the arrays of photodiodes of the SiPMs). The backend system 42 can further generate PET images of ROIs using the scanner 12 and the individual energy windows 44. The backend system 42 is typically remote from the scanner 12 and includes a plurality of modules 46 to carry out the forgoing functionality.

A control module 48 of the backend system 42 controls overall operation of the backend system 42. The control module 48 suitably displays a graphical user interface (GUI) to a user of the backend system 42 using a display device 50 of the backend system 42. Further, the control module 48 suitably allows the operator to interact with the GUI using a user input device 52 of the backend system 42. The user can interact with the GUI to instruct the backend system 42 to coordinate imaging of a ROI.

To generate a PET image of a ROI using the scanner 12 and the individual energy windows 44, the ROI is injected with a radionuclide which emits positrons and is positioned within the examination volume 16 (e.g., using the subject support 18). Typically, a pair of annihilation gammas is produced by a positron annihilation event in the examination region 16, where each annihilation gamma of the pair travels in approximately opposite directions. A data acquisition module 54 of the backend system 42 is then used to acquire emission data describing gamma photons received by the detectors 14.

The data acquisition module 54 of the backend system 42 controls the scanner 12 to perform PET scans of the examination region 16. During a PET scan, the data acquisition module 54 monitors each of the detectors 14 for a gamma event. Each gamma event corresponds to the deposition of energy by a gamma photon in one of the scintillators 20. When a gamma event is detected, the data acquisition module 54 time stamps the event. Further, the data acquisition module 54 records both an estimate of the location where the event occurred on the detectors 14 (corresponding to a pixel) and an estimate of the energy of the event. Where the sensors 24 correspond to PMTs, the energy corresponds to the integrated area under an energy pulse received from the PMTs. Where the sensors 24 correspond to the SiPMs, the energy corresponds to a photon count (i.e., a count of the cells of the photodiode array for the detecting pixel that triggered) of the light pulse.

After data acquisition, an event verification module 56 of the backend system 42 is used to filter the gamma events of the emission data using the individual energy windows 44. Namely, each detected gamma event of the emission data that falls outside the energy window 30 of the pixel that detected the gamma event is filtered out of the emission data. Put another way, the emission data is filtered so all the gamma events of the emission data meet the following condition:

$$LLD_{ij} < E_{ij} < ULD_{ij},$$

where i and j identify one of the pixels by the column and row of the detector that detected the gamma event, $LLD_{ij}$ describes the LLD for the pixel i, j, $ULD_{ij}$ describes the ULD for the pixel i, j, and $E_{ij}$ describes the energy of a gamma detected by the pixel i, j. Thus, when pixel i, j detects a gamma photon (specifically, a deposition of energy by the gamma photon), the energy window for the individual pixel i, j is applied. In this manner, the applied energy window for each event is determined by the pixel that detects the event. The application of individualized energy windows can be implemented in either firmware and/or parallel processing software.

As should be appreciated, the foregoing assumes that substantially all of the energy of each detected gamma photon is detected by a single pixel, thereby triggering a single representative event. However, gammas can deposit their energy across multiple pixels, and thereby triggering multiple gamma events. The true energy of a gamma photon is the summation of all the energy depositions. Hence, it is contemplated that the event verification module 56 clusters the gamma events before the filtering so multiple gamma events in response to a common gamma photon are combined into a common gamma event.

After filtering, the event verification module 56 is used to determine coincident events from the filtered emission data by pairing gamma events within a specified time difference of each other. The specified time difference is small enough to ensure the gamma events are triggered by gammas from the same annihilation event. Each coincident event defines a line of response (LOR), which can be used for image reconstruction. The LORs of detected coincident events are typically stored in a list in one or more storage memories 58 along with the time stamps of the corresponding gammas.

A reconstruction module 60 of the backend system 42 reconstructs LORs from the event verification module 56 into a PET image of the ROI. Any number of well know algorithms for reconstructing the LORs into PET images are contemplated. For example, the reconstruction module 60 can be configured to reconstruct the LORs into an amyloid PET image. The PET images are suitably stored in the one or more storage memories 58 and/or displayed to a user using the display device 50.

For the sake of simplicity, random correction, attenuation correction, cascade gamma correction, scatter correction and the like were not discussed. However, it is to be appreciated that such correction can be employed with the PET imaging system 10. For example, the PET imaging system 10 can employ statistical approaches to scatter correction using single-scatter simulation (SSS) and/or Monte Carlo simulation.

The foregoing dealt with the generation of an image representation of a ROI in the examination region 16 through application of the energy windows 44 individualized for the pixels of the detectors 14. These individualized energy windows 44 are suitably determined before the generation of the image representation during calibration of the detectors 14. In that regard, to calibrate the detectors 14 and determine the individual energy windows 44 for the pixels, a calibration phantom, such as a uniform point source, which emits gamma photons, is placed at the isocenter of the examination region 16. The data acquisition module 54 of the backend system 42 is then used to obtain data describing the energy spectrum for each pixel of the detectors 14. An energy spectrum describes the relationship between gamma event counts and the energy of the events. A gamma event corresponds to depositions of energy in the detectors 14 by a gamma photon.

The data acquisition module 54 monitors each of the detectors 14 for a gamma event. When an event is detected, the data acquisition module 54 time stamps the event. Further, the data acquisition module 54 records both an estimate of the location (e.g., pixel) where the event occurred and an estimate of the energy of the event. Where PMTs are used, the energy is typically determined by integrating the area under an energy pulse resulting from the event. Where solid state detectors, such as SiPMs, are used, the energy is proportional to a count of light photons.

After the data describing the energy spectra of the pixels of the detectors 14 are determined, an energy calibration module 62 of the backend system 42 determines scaling factors to align the centroids of the individual pixels, or the centroids of the detectors 14, to the known energy of the gamma rays created in a PET annihilation event (e.g., 511 keV). Further, the energy calibration module 62 determines an individual energy window for each pixel of the detectors 14.

To determine an individual energy window for each pixel of the detectors 14, each energy spectrum is fitted with a modified Gaussian function modeling the relationship between counts and energy, with energy being the dependent variable. The modified Gaussian function can be written as follows:

$$f(x) = a + bx + cx^2 + \frac{1}{\sigma\sqrt{2\pi}} e^{-\frac{(x-\mu)^2}{\sigma^2}},$$

where x is energy, f(x) is counts, a, b, and c are constants, $\mu$ is the expected value and $\sigma$ is the variance. The constants a, b, c, the expected value $\mu$ and the variance $\sigma$ are suitably determined using a derivative based optimization in the least square sense, which can be very accurate in representing the original noisy energy spectrum. However, other approaches can be employed. After fitting an energy spectrum with a modified Gaussian function, trend lines are fit to both sides of the Gaussian, typically in the least square sense. These two trend lines represent the trend of the energy spectrum. The intersections of these two trend lines with the x axis (corresponding to energy) are then used as the lower level discriminator (LLD) and the upper level discriminator (ULD) for the pixel. The individual energy windows 44 (i.e., the LLDs and the ULDs) are suitably stored in the storage memories 58 of the backend system 42.

Figure 5:
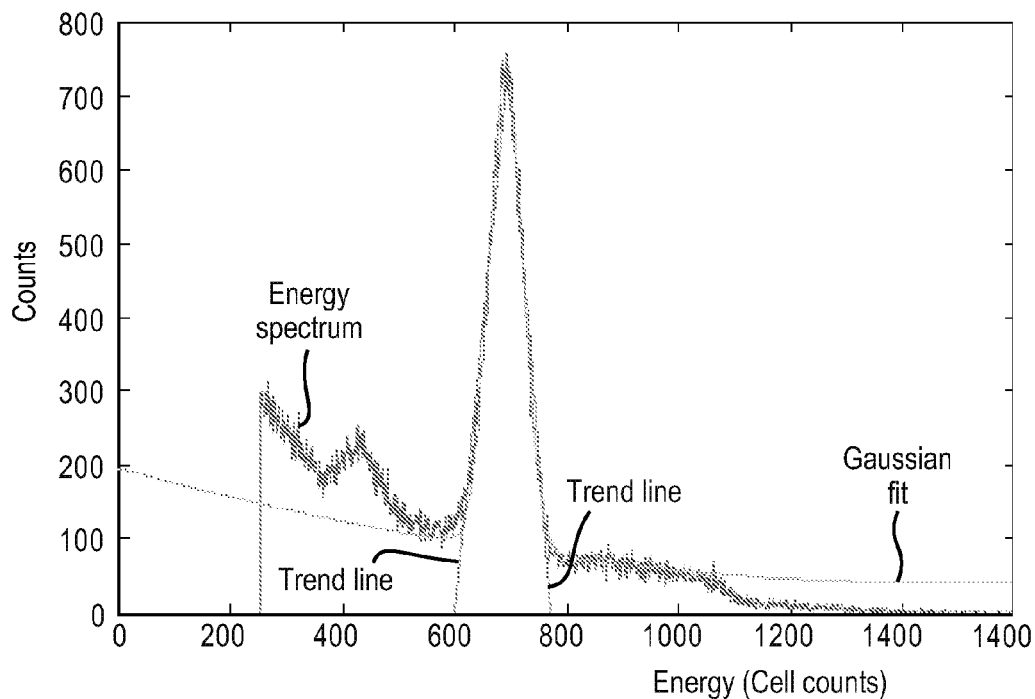
FIG. 5 illustrates a typical energy spectrum of a silicon photomultipliers (SiPM) with a cerium-doped lutetium yttrium orthosilicate (LYSO) scintillator, the modified Gaussian fit for the energy spectrum and the trend lines fit to the modified Gaussian fit.

FIG. 5 illustrates a typical energy spectrum of a SiPM with a LYSO scintillator, the modified Gaussian fit for the energy spectrum and the trend lines fit to the modified Gaussian fit. As can be seen, the trend lines interest with the x axis around 600 and 780. These two energy levels define the LLD and the ULD of the energy window, respectively, for the pixel to which the energy spectrum belongs.

Figure 6:
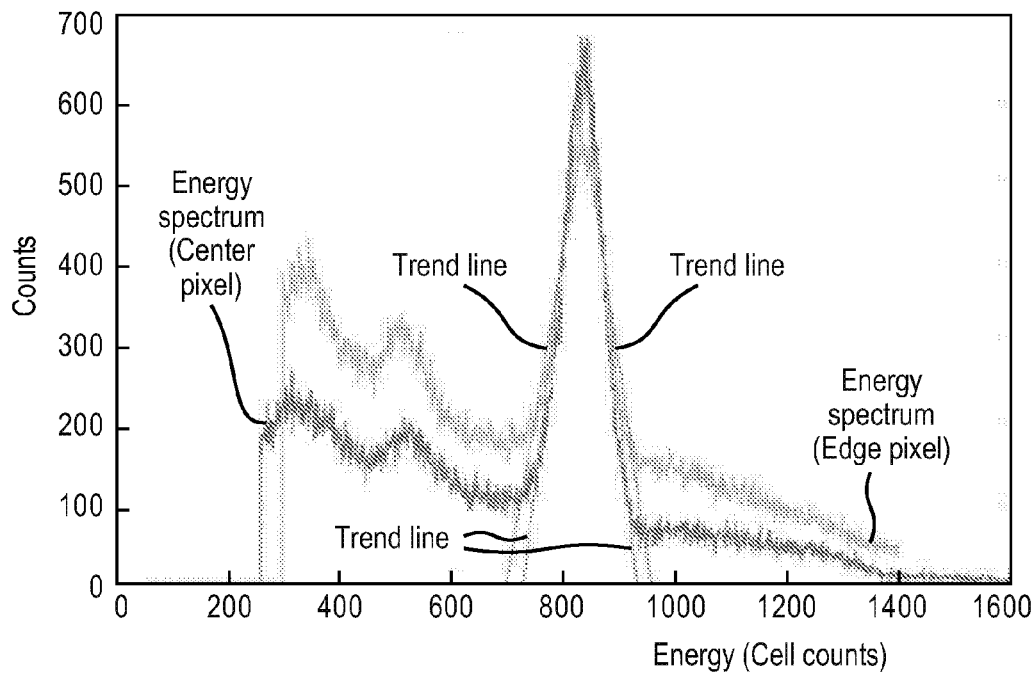
FIG. 6 illustrates the determination of energy windows for two different energy spectra and the resulting energy windows.

FIG. 6 illustrates the determination of energy windows for two different energy spectra and the resulting LLDs and ULDs. The first energy spectrum corresponds to a center pixel, and the second energy spectrum corresponds to an edge pixel. As can be seen, the edge pixel has more background noise and a lower peak with a wider full width half max (FWHM). Hence, the LLDs and ULDs for the two energy spectra are different. The LLD for the center pixel is 87% of the energy of the peak, and the ULD for the center pixel is 112% of the energy of the peak. In contrast, the LLD for the edge pixel is 83% of the energy of the peak, and the ULD for the edge pixel is 117% of the energy of the peak. With the two individualized energy windows, both pixels get the best possible number of true counts according to the energy. This improves the overall system's ability of scatter rejection.

While the foregoing dealt with the energy spectra of singles (i.e., any single gamma event), it is also contemplated that coincidence energy spectra can also be employed to generate the energy windows 44. To that end, the energy calibration module 62 filters the energy spectra to remove gamma events which do not correspond to coincidence events before determining the energy windows. A coincident event corresponds to the detection of a pair of gammas within a specified time difference of each other, the specified time difference small enough to ensure the gammas are from the same annihilation event. Hence, the filtering includes removing singles that are not within the specified time difference of other singles.

Further, while the foregoing dealt with determining the energy windows 44 for a single energy level (e.g., 511 keV), it is to be appreciated that the energy windows 44 are suitably tailored to the energy level used during imaging. Hence, it is preferable to determine energy windows for each energy level to be used during imaging. In one instance, this is accomplished by performing the foregoing approach for each energy level. However, this can be time consumer. In another instance, the energy windows for one energy level are determined according to the foregoing approach. Thereafter, the energy windows for other energy levels are extrapolated using the known relationship between energy levels. This known relationship can be determined, for example, experimentally.

Each of the plurality of modules 46 can be embodied by processor executable instructions, circuitry (i.e., processor independent), or a combination of the two. The processor executable instructions are stored on at least one program memory 64 of the backend system 42 and executed by at least one processor 66 of the backend system 42. As illustrated, the plurality of modules 46 is embodied by processor executable instructions. However, as is to be appreciated, variations are contemplated. For example, the data acquisition module 54, or another other module, can be embodied by circuitry, a field-programmable gate array (FPGA), an application-specific integrated circuit (ASIC), or a combination of the foregoing.

Figure 7:
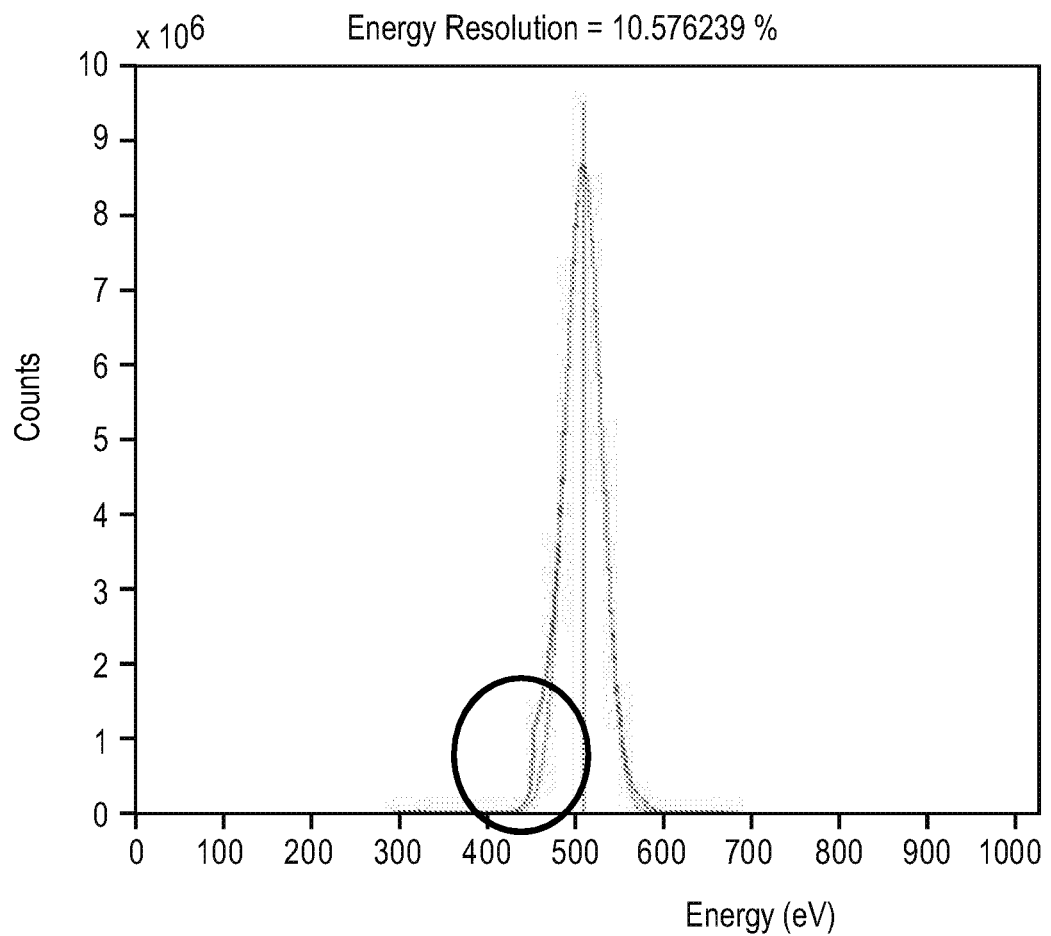
FIG. 7 illustrates both the energy spectrum of a PET imaging system using individualized energy windows and the energy spectrum of a known PET imaging system.

With reference to FIG. 7, a graph illustrates an energy spectrum typical of known PET imaging systems and an energy spectrum typical of PET imaging systems, such as the PET imaging system 10, using individualized energy windows, as described above. The energy spectra are determined by filtering out events which do not fall within their respective energy windows and by filtering out singles which do not belong to coincidence events. For known PET imaging systems, a common energy window is used for all events. As can be seen, the energy spectrum using individualized energy windows has a slant line instead of a hard cut at front, as marked inside the circle.

Figure 8:
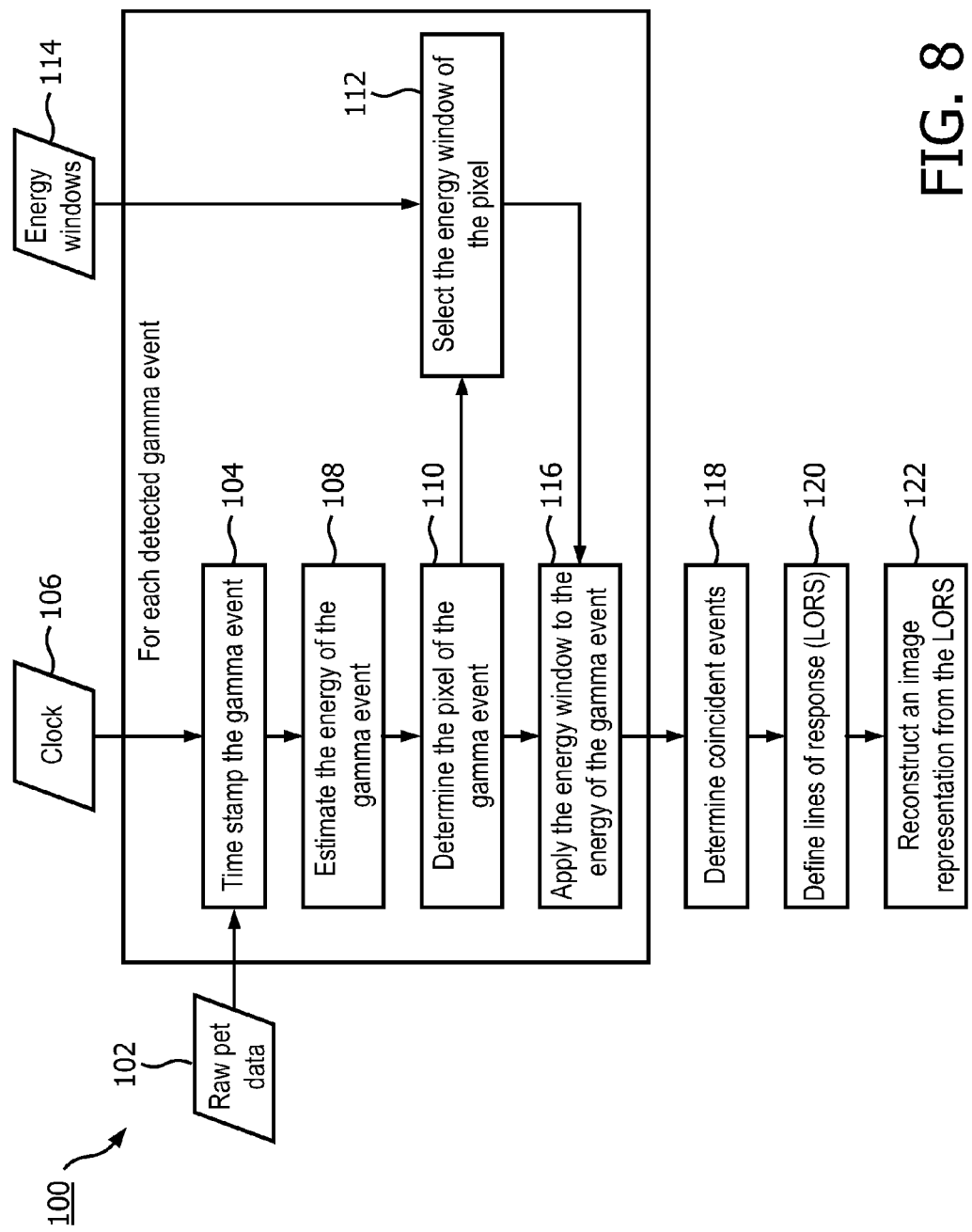
FIG. 8 illustrates a method for generating an image representation of a region of interest (ROI) using individualized energy windows for scatter rejection.

With reference to FIG. 8, a method 100 for generating a PET image of a ROI is provided. The method 100 is suitably embodied by processor executable instructions stored on the program memory 64 of the backend system 42 and executed by the at least one processor 66 of the backend system 42. However, it is also contemplated that the constituent actions (or illustrated blocks) can be implemented wholly and/or partially without the use of programmable processors. Further, the constituent actions (or illustrated blocks) can be independent "units" or "modules", each unit or module corresponding to a hardware and/or software performing the corresponding functions.

The method 100 includes receiving raw PET data 102 from the detectors 14 of the PET scanner 12, which is monitored for gamma events. For each detected gamma event, the gamma event is time stamped 104 using clock data 106. The energy of the gamma event is further estimated 108. Where the detectors 14 employ PMTs, the energy is estimated by integrating the area under the energy curve received from the detectors 14. Where the detectors 14 employ SiPMs, the energy is estimated by counting the cells (i.e., photodiodes) fired in response to the gamma event. The pixel of the gamma event is further determined 110. Where the detectors 14 employ PMTs, Anger logic is used to determine the pixel. Where the detectors 14 employ SiPMs, pixel simply corresponds to the pixel of the SiPMs generating triggering the gamma event. After determining the pixel of the gamma event, the energy window of the pixel is selected 112 from a plurality of predetermined energy windows 114, typically determined during calibration of the detectors 12. The selected energy window is applied 116 to the energy of the gamma event and the gamma event is discarded if the energy of the gamma event falls outside the energy window. Otherwise, the gamma event passes through the energy window.

Using the filtered gamma events (i.e. those gamma events passing through their energy windows), coincidence events are determined 118. A coincident event corresponds to the detection of a pair of gammas within a specified time difference of each other, the specified time difference small enough to ensure the gammas are from the same annihilation event. Further, LORs are defined 120 using the determined coincident events. The defined LORs are then used to reconstruct 122 an image representation of the ROI.

Figure 9:
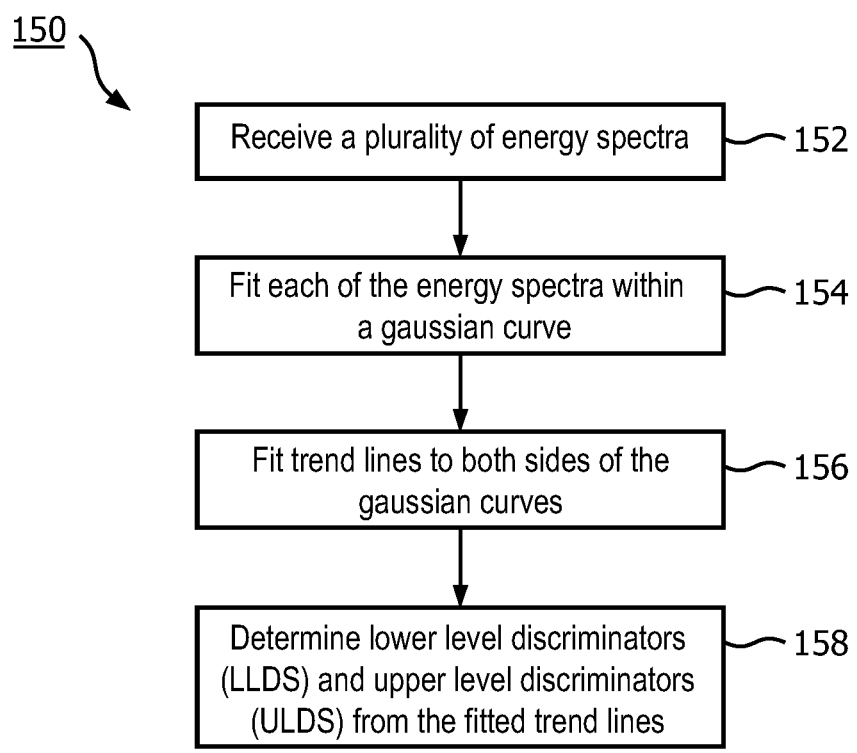
FIG. 9 illustrates a method for determining individualized energy windows for scatter rejection.

With reference to FIG. 9, a method 150 for determining individualized energy windows for scatter rejection is provided. The method 150 is suitably embodied by processor executable instructions stored on the program memory 64 of the backend system 42 and executed by the at least one processor 66 of the backend system 42. However, it is also contemplated that the constituent actions (or illustrated blocks) can be implemented wholly and/or partially without the use of programmable processors. Further, the constituent actions (or illustrated blocks) can be independent "units" or "modules", each unit or module corresponding to a hardware and/or software performing the corresponding functions.

The method 100 includes receiving 152 an energy spectrum for each pixel of the detectors 14. The energy spectra are suitably generated from gamma rays emitted by a calibration phantom. The energy spectrum of each pixel is fit 154 with a Gaussian curve using, for example, the modified Gaussian function described above. Further, trend lines are fit 156 to both sides of the Gaussian curves of the energy spectra. Once the trend lines are fitted, LLDs and ULDs are determined 158 from the fitted trend lines. A pair of an LLD and a ULD from the same Gaussian curve defines an energy window for the pixel which detected the energy spectrum.

While the foregoing dealt with individualized energy windows for pixels, individualized energy windows can be determined for crystals, bins (e.g., for continuous crystals), groupings of pixels (e.g., 4×4 groupings), and any other units for which counts can be localized. Further, although the individualized energy windows dealt with PET imaging, those skilled in the art will appreciate that the individualized energy windows can be applied to single-photon emission computed tomography (SPECT) imaging.

As used herein, a memory includes one or more of: a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; and the like. Further, as used herein, a processor includes one or more of a microprocessor, a microcontroller, a graphic processing unit (GPU), and the like; a user input device includes one or more of a mouse, a keyboard, a touch screen display, a button, a switch, a voice recognition engine, and the like; and a display device includes one or more of a liquid crystal display (LCD) display, a light emitting diode (LED) display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical nuclear imaging system comprising:
   a plurality of pixels which detect radiation events and estimate the energy of the detected radiation events;
   a memory which stores a plurality of energy windows, the energy windows corresponding to the pixels;
   an event verification module which windows the radiation events with the energy windows corresponding to the detecting pixels;
   a reconstruction processor which reconstructs the windowed radiation events into an image representation.

2. The medical nuclear imaging system according to claim 1, wherein the energy spectra describe the relationship between event counts and event energy, an event corresponding to the deposition of energy by a gamma photon.

3. The medical nuclear imaging system according to claim 1, wherein the medical nuclear imaging system is one of a single-photon emission computed tomography (SPECT) imaging system and a positron emission tomography (PET) imaging system.

4. The medical nuclear imaging system according to claim 1, further including:
   a plurality of detectors including silicon photomultipliers (SiPMs), the SiPMs including the pixels.

5. The medical nuclear imaging system according to claim 1, wherein the radiation events are gamma events.

6. The medical nuclear imaging system according to claim 1, further including:
   an energy calibration module configured to:
      receive calibration energy spectra corresponding to the plurality of pixels, the calibration energy spectra generated from gamma photons from a calibration phantom;
      fit the calibration energy spectra with Gaussian curves;
      fit trend lines to both sides of the Gaussian curves of the calibration energy spectra; and
      determine lower level discriminators (LLDs) and upper level discriminators (ULDs) from the fitted trend lines, the LLDs and the ULDs defining the energy windows.

7. The medical nuclear imaging system according to claim 6, wherein the energy calibration module is further configured to:
   determine the LLDs by identifying the energy of trend lines on the lower energy sides of the Gaussian curves at zero event counts; and
   determine the ULDs by identifying the energy of trend lines on the higher energy sides of the Gaussian curves at zero event counts.

8. The medical nuclear imaging system according to claim 6, wherein the pixels generate the calibration energy spectra from only gamma events of coincidence events.

9. The medical nuclear imaging system according to claim 6, wherein the energy calibration module is further configured to:
   for a plurality of energy levels to which the pixels can be calibrated, determine individual energy windows for the pixels.

10. A medical nuclear imaging method comprising:
    detecting radiation events by a plurality of pixels;
    estimating the energy of the detected radiation events;
    receiving a plurality of energy windows, wherein the pixels correspond to the energy windows;
    windowing the radiation events with the energy windows corresponding to the detecting pixels; and
    reconstructing the windowed radiation events into an image representation.

11. The medical nuclear imaging method according to claim 10, further including:
    detecting the radiation events by silicon photomultipliers (SiPMs), which include the plurality of pixels.

12. The medical nuclear imaging method according to claim 10, further including:
    receiving calibration energy spectra corresponding to the plurality of pixels, the calibration energy spectra generated from gamma photons from a calibration phantom;
    fitting the calibration energy spectra with Gaussian curves;
    fitting trend lines to both sides of the Gaussian curves of the calibration energy spectra; and
    determining lower level discriminators (LLDs) and upper level discriminators (ULDs) from the fitted trend lines, the LLDs and the ULDs defining the energy windows.

13. The medical nuclear imaging method according to claim 12, further including:
    determining the LLDs by identifying the energy of trend lines on the lower energy sides of the Gaussian curves at zero event counts; and
    determining the ULDs by identifying the energy of trend lines on the higher energy sides of the Gaussian curves at zero event counts.

14. The medical nuclear imaging method according to claim 12, further including:
    generating the calibration energy spectra from only gamma events of coincidence events; and
    for a plurality of energy levels to which the pixels can be calibrated, determining individual energy windows for the pixels.

15. A non-transitory computer readable medium carrying software which controls one or more processors to perform the method according to claim 10.

* * * * *